United States Patent
Lorio

(10) Patent No.: US 10,925,751 B2
(45) Date of Patent: Feb. 23, 2021

(54) VERTICALLY EXPANDABLE INTERVERTEBRAL CAGE, DEPLOYMENT DEVICE, AND METHODS OF USING

(71) Applicant: EIT Emerging Implant Technologies GmbH, Wurmlingen (DE)

(72) Inventor: Morgan Packard Lorio, Bristol, TN (US)

(73) Assignee: EIT Emerging Implant Technologies GmbH, Wurmlingen (DE)

( * ) Notice: Subject to any disclaimer, the term of this patent is extended or adjusted under 35 U.S.C. 154(b) by 285 days.

(21) Appl. No.: 16/024,313

(22) Filed: Jun. 29, 2018

(65) Prior Publication Data
US 2018/0303628 A1 Oct. 25, 2018

Related U.S. Application Data

(63) Continuation of application No. 14/773,368, filed as application No. PCT/US2014/018772 on Feb. 26, 2014, now Pat. No. 10,022,240.
(Continued)

(51) Int. Cl.
*A61F 2/44* (2006.01)
*A61F 2/46* (2006.01)
*A61F 2/30* (2006.01)

(52) U.S. Cl.
CPC ............ *A61F 2/447* (2013.01); *A61F 2/4611* (2013.01); *A61F 2/4603* (2013.01);
(Continued)

(58) Field of Classification Search
CPC ...................................... A61F 2/44–2002/4495
See application file for complete search history.

(56) References Cited

U.S. PATENT DOCUMENTS

| | | | | |
|---|---|---|---|---|
| 5,693,100 A | * | 12/1997 | Pisharodi | A61F 2/442 623/17.16 |
| 5,782,832 A | * | 7/1998 | Larsen | A61F 2/30742 623/17.11 |
| 6,039,761 A | * | 3/2000 | Li | A61F 2/441 623/17.16 |
| 6,126,689 A | * | 10/2000 | Brett | A61F 2/4455 623/17.16 |
| 6,409,766 B1 | * | 6/2002 | Brett | A61F 2/4455 623/17.16 |

(Continued)

FOREIGN PATENT DOCUMENTS

WO WO2012135764 A1 4/2012
WO 2014/035835 A1 3/2014

OTHER PUBLICATIONS

International Search Report and Written Opinion in Application No. PCT/US2014/018772, dated Jun. 2, 2014 in 10 pages.

*Primary Examiner* — Zade Coley
(74) *Attorney, Agent, or Firm* — BakerHostetler

(57) ABSTRACT

A vertically expandable intervertebral cage, deployment devices, and methods for using the same. The intervertebral cage can include a circuitous body at least partially enclosing an interior volume. The intervertebral cage can also include a front panel which can be formed into a wedge for facilitating implantation of the intervertebral cage into an intervertebral space. The intervertebral cage can be converted from an undeployed configuration, wherein the height of the intervertebral cage is reduced, to a deployed configuration, wherein the height of the intervertebral cage is increased to support end plates of the vertebrae. The intervertebral cage can be converted from the undeployed configuration to a deployed configuration by using a deployment device such as an implantation device and a guide wire. The deployment device can be used to impart a force upon the cage.

20 Claims, 9 Drawing Sheets

Related U.S. Application Data

(60) Provisional application No. 61/778,220, filed on Mar. 12, 2013.

(52) U.S. Cl.
CPC ........... *A61F 2002/30014* (2013.01); *A61F 2002/30092* (2013.01); *A61F 2002/30153* (2013.01); *A61F 2002/30471* (2013.01); *A61F 2002/30476* (2013.01); *A61F 2002/30484* (2013.01); *A61F 2002/30517* (2013.01); *A61F 2002/30556* (2013.01); *A61F 2002/30593* (2013.01); *A61F 2002/4627* (2013.01); *A61F 2310/00017* (2013.01); *A61F 2310/00023* (2013.01)

(56) References Cited

U.S. PATENT DOCUMENTS

| | | | |
|---|---|---|---|
| 6,488,710 B2* | 12/2002 | Besselink | A61F 2/4611 623/17.15 |
| 2006/0142858 A1* | 6/2006 | Colleran | A61F 2/4465 623/17.11 |
| 2008/0183204 A1* | 7/2008 | Greenhalgh | A61F 2/4611 606/198 |
| 2012/0083887 A1* | 4/2012 | Purcell | A61F 2/4611 623/17.16 |
| 2012/0083889 A1* | 4/2012 | Purcell | A61F 2/4455 623/17.16 |
| 2012/0123546 A1* | 5/2012 | Medina | A61F 2/447 623/17.16 |

* cited by examiner

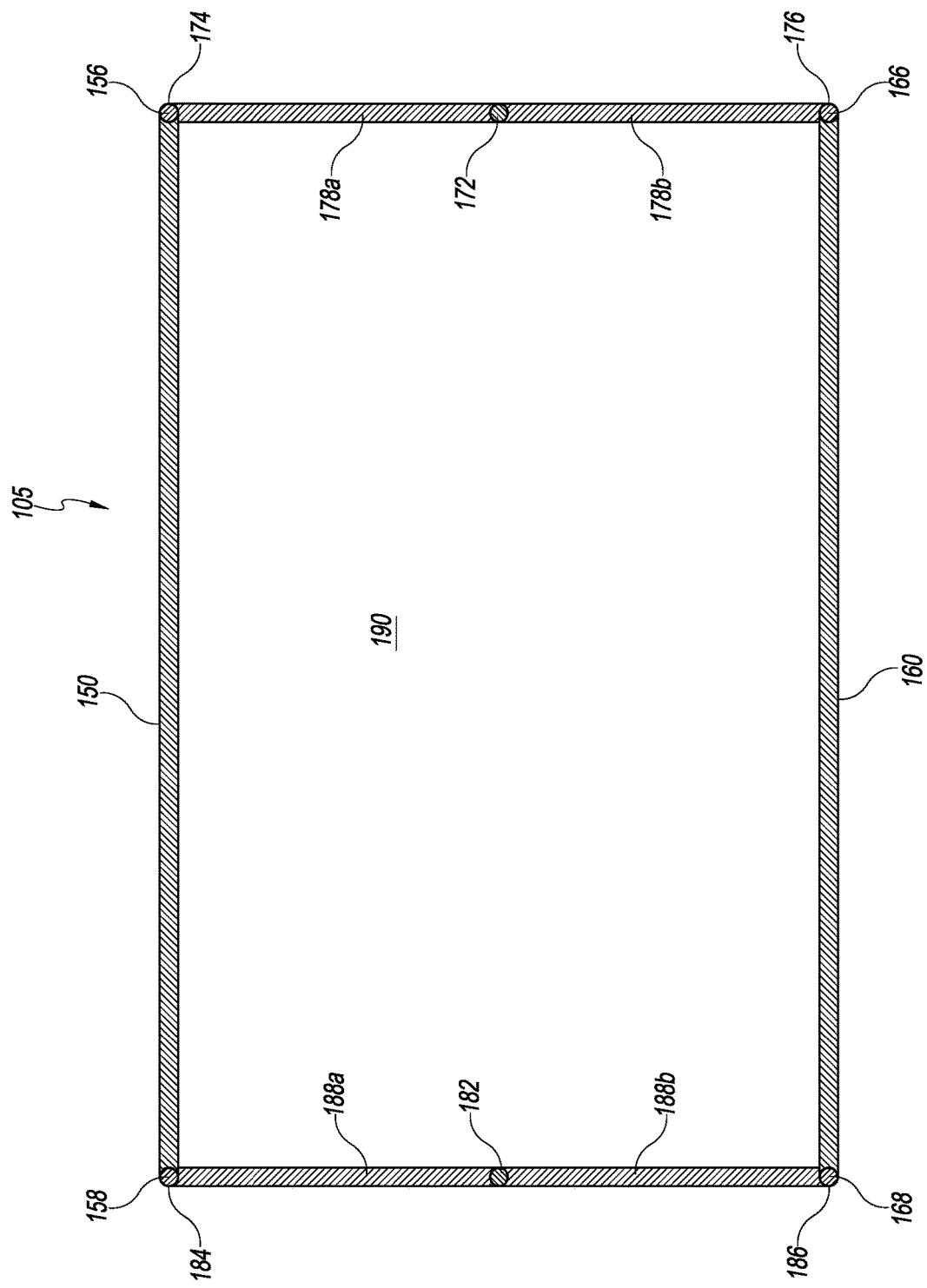

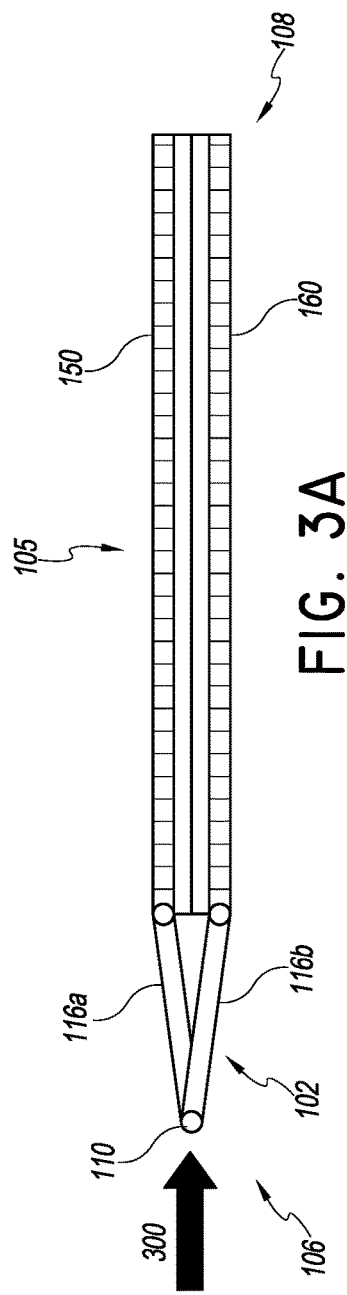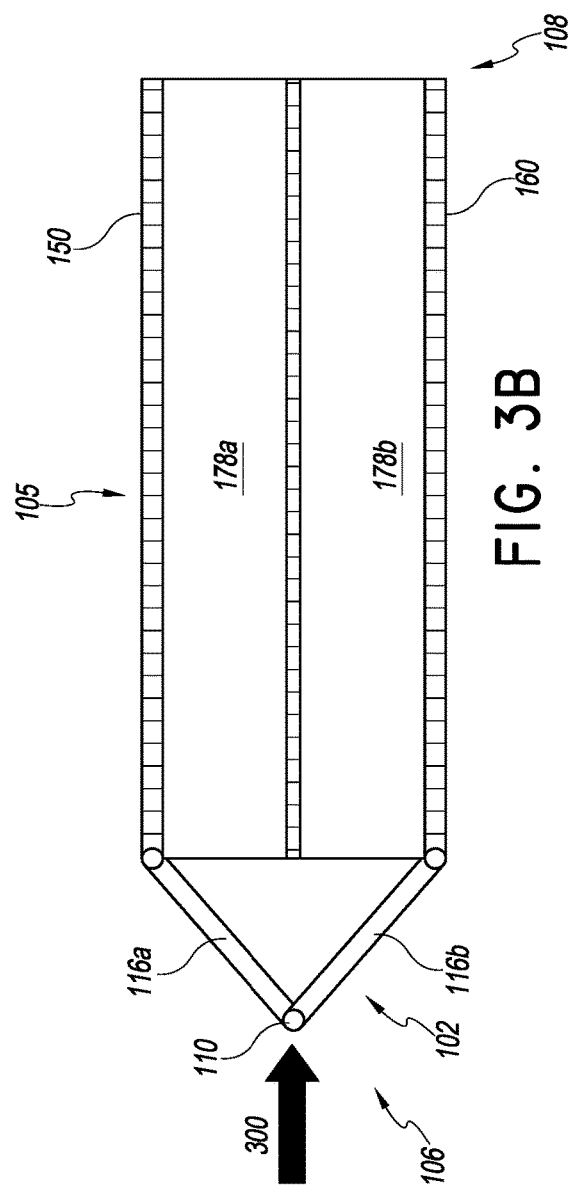

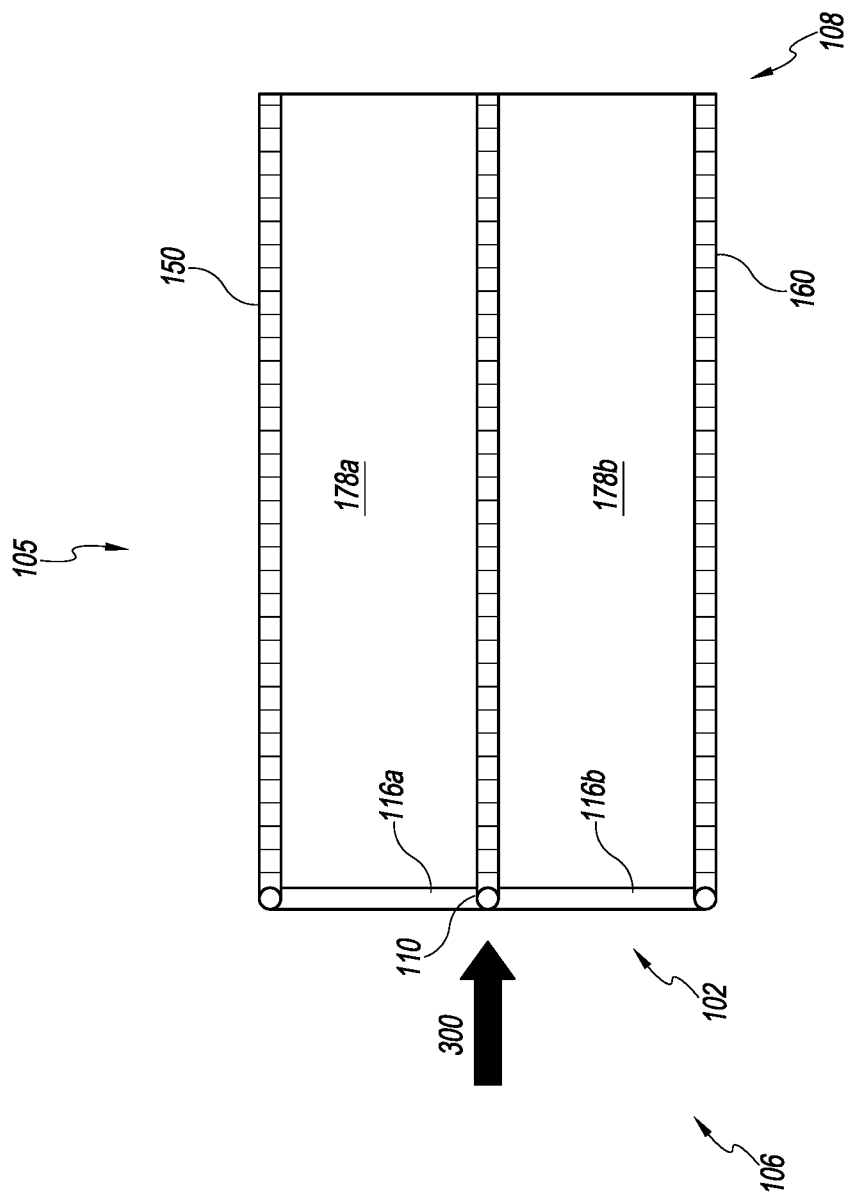

VERTICALLY EXPANDABLE INTERVERTEBRAL CAGE, DEPLOYMENT DEVICE, AND METHODS OF USING

RELATED APPLICATIONS

The present application is a continuation application of U.S. patent application Ser. No. 14/773,368, filed Feb. 26, 2015, which is a nation a stage application under 35 U.S.C. 371 of PCT Application No. PCT/US2014/018772, filed Feb. 26, 2014, which claims priority to U.S. Provisional Application No. 61/778,220 filed Mar. 12, 2013, titled VERTICALLY EXPANDABLE INTERVERTEBRAL CAGE, the entire contents of each are hereby expressly incorporated by reference.

BACKGROUND

Field

The present application relates to the field of spinal treatment devices, systems and methods, and more specifically, to intervertebral spinal implants and methods of using the same.

Background

Current intervertebral devices are designed using three major principles: the anatomical limitations of the surgical approach, optimization of bone graft volume to promote bone fusion, and optimization of the device contact with vertebral end plates to resist subsidence. Many current devices are generally static in that they cannot change shape or volume. Thus, many current devices are limited by anatomy and technique and consequently may not provide optimal bone graft volume or surface contact.

Other current intervertebral devices can change their shape and volume; however, these devices lack rigid components. As a result of this, while these devices are able to change their shape and/or volume, these devices do not provide for stable contact with vertebral end plates. Accordingly, there is a need for intervertebral devices which can change their shape and volume while providing stable contact with vertebral end plates.

SUMMARY

Certain embodiments of the present application relate to intervertebral implants and methods of using the same. Some embodiments relate to an intervertebral cage that can be configured for positioning between two vertebrae and specifically between two vertebral end plates. In some embodiments, the intervertebral cage can be configured for expansion generally orthogonal to the vertebral end plates. That is, the intervertebral cage can be expandable at least a direction towards a vertebral end plate. In some embodiments, the intervertebral cage can also be configured for expansion generally parallel to the vertebral end plates.

In some embodiments, the intervertebral cage can include a circuitous body at least partially enclosing an interior volume. The circuitous body can include a top panel having a distal edge and at least two side edges, a bottom panel having a distal edge and at least two side edges, and at least two side panels, each having a top edge and a bottom edge. The side panel may include at least one hinge dividing the side panel into at least two side panel sections. The top edges of the side panels may be rotatably attached to the side edges of the top panel along a hinge. The bottom edges of the side panels may be rotatably attached to the side edges of the bottom panel along a hinge. In some embodiments, the intervertebral cage can include a front panel having a top edge and a bottom edge, wherein the front panel additionally comprises at least one hinge dividing the front panel into at least two front panel sections. The top edge of the front panel may be rotatably attached to the distal edge of the top panel and the bottom edge of the front panel may be rotatably attached to the distal edge of the bottom panel. In some embodiments, in a first position, the top panel and bottom panel can be separated by a first distance and the front panel can form a leading wedge. In some embodiments, in a second position, the top panel and bottom panel can be separated by a second distance, the second distance being greater than the first distance.

In some embodiments, the intervertebral cage can include a circuitous body which can include a plurality of panels partially enclosing an interior volume, the plurality of panels including at least a top panel, a bottom panel, and two side panels, wherein each of the panels of the plurality of panels are rotatably attached to adjacent panels along hinges. In some embodiments, the intervertebral cage can also include a front panel having a first front panel section rotatably attached to a second front panel section, the front panel being rotatably attached to at least two panels of the plurality of panels of the circuitous body. In some embodiments, in a first position, a distal-most part of the front panel protrudes distally from the circuitous body. In some embodiments, in a second position, the distal-most part of the front panel protrudes less distally from the circuitous body.

Some embodiments relate to methods of using an expandable intervertebral cage. In some embodiments, the method can include positioning the intervertebral cage in the intervertebral disc space, wherein the intervertebral cage is configured to be moved from a first position to a second position and wherein the intervertebral cage comprises a circuitous body and a front panel, forming a wedge with the front panel and applying a force on one or more panels of the intervertebral cage. In some embodiments, the circuitous body can include a plurality of panels.

Some embodiments relate to intervertebral cage systems. In some embodiments, the system can include an intervertebral cage which can include a circuitous body having a plurality of panels partially enclosing an interior volume. The plurality of panels can include at least a top panel, a bottom panel, and two side panels. Each of the panels of the plurality of panels can be rotatably attached to adjacent panels along hinges. In some embodiments, the intervertebral cage of the system can include a front panel having a first front panel section rotatably attached to a second front panel section. The front panel can be rotatably attached to at least two panels of the plurality of panels of the circuitous body. In some embodiments, the intervertebral cage can be configured so that, in a first position, a distal-most part of the front panel protrudes distally from the circuitous body. In some embodiments, the intervertebral cage can be configured so that, in a second position, the distal-most part of the front panel protrudes less distally from the circuitous body. In some embodiments, the system can also include a deployment device configured to apply a force to convert the intervertebral cage from the first position to the second position.

BRIEF DESCRIPTION OF THE DRAWINGS

FIG. 2C illustrates a cross-sectional view, along line A-A, of the intervertebral cage of FIG. 1 in a third position.

FIG. 3A illustrates a side elevation view of the intervertebral cage of FIG. 1 in a first position.

FIG. 3B illustrates a side elevation view of the intervertebral cage of FIG. 1 in a second position.

FIG. 3C illustrates a side elevation view of the intervertebral cage of FIG. 1 in a third position.

DETAILED DESCRIPTION

Embodiments are shown of a vertically expandable intervertebral cage configured for positioning between two vertebrae and specifically between two vertebral end plates. The vertically expandable intervertebral cage is configured to have at least two different configurations. In a first or undeployed configuration, the apparatus is configured to have a reduced dimension in the vertical direction (i.e., an axis perpendicular to the plane of a vertebral end plate) or a reduced height which thereby facilitates the process of inserting the apparatus into the vertebral space during an implantation procedure. In a second or deployed configuration, the apparatus is configured to have an increased dimension in the vertical dimension or an increased height. In this deployed configuration, the apparatus is configured to maintain spacing between the two vertebral end plates at a desired height. Embodiments of the device can have different vertical dimensions or heights based upon the application. The intervertebral cage as described herein can be "space-agnostic" in the sense that it can be used for multiple spinal fusion techniques including transforaminal lumbar interbody fusion (TLIF) and lateral lumbar interbody fusion (XLIF).

Intervertebral Cage

Figure 1:
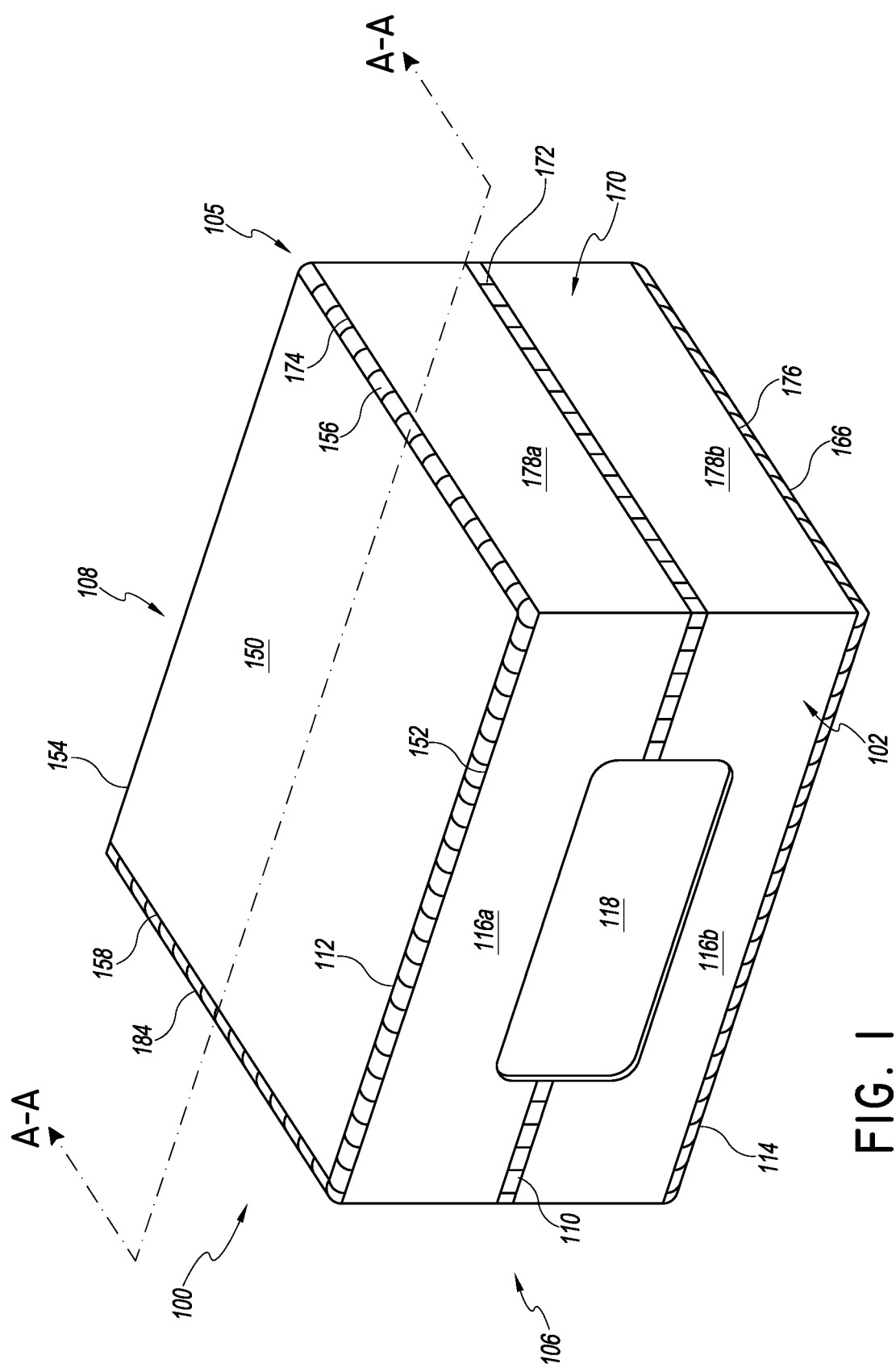
FIG. 1 illustrates a perspective view of an embodiment of a vertically expandable intervertebral cage.

FIG. 1 is an illustration of an embodiment of the intervertebral cage 100 in a deployed configuration. The intervertebral cage 100 has both a front panel 102 and a circuitous body 105. In a deployed configuration, front panel 102 is configured to provide structural support, in the form of a strut, for the cage 100. In one embodiment, the front panel 102 includes a hinge 110 positioned equidistant from the top edge 112 and the bottom edge 114 which subdivides the front panel 102 into both a top section 116a and a bottom section 116b. In other embodiments, the hinge 110 may be placed closer to the top edge 112 or to the bottom edge 114 depending upon the geometry desired in the undeployed and deployed configurations. Furthermore, in yet other embodiments, more than one hinge can be included on the front panel 102.

In some embodiments, the top section 116a and the bottom section 116b are separate units which are rotatably attached at hinge 110 to form front panel 102. In those embodiments, rotatable attachment of the top and bottom sections 116a, 116b can be accomplished through attachment mechanisms such as, but not limited to, pin-hinge assemblies, elastic adhesives, attachment to other materials allowing for elastic deformation, or other hinging mechanisms used in the art. In another embodiment, the top section 116a and the bottom section 116b are integral and form a single unit. In that embodiment, the hinge 110 is formed via a reduced thickness (i.e., a living hinge) of the front panel 102 along the hinge 110 which is configured to allow deformation along hinge 110.

In one embodiment, such as that illustrated in FIG. 1, the front panel 102 has an aperture 118 substantially centered on the front panel 102. In other embodiments, the front panel 102 has multiple apertures located on both the top section 116a and bottom section 116b. Aperture 118 can be configured to allow a distal part of an implantation device to enter through the trailing end 108 of the intervertebral cage 100 and pass through aperture 118 such that the distal part of the implantation device is distal the front panel 102. In embodiments with multiple apertures on the top section 116a and the bottom section 116b, the apertures can be configured to allow a guide wire to be inserted through the trailing end 108 of the intervertebral cage 100 through a first aperture and returned to the trailing end 108 through a second aperture. The implantation device or guide wire can be used to apply the force to convert the intervertebral cage 100 from an undeployed configuration to a deployed configuration.

Figure 7:
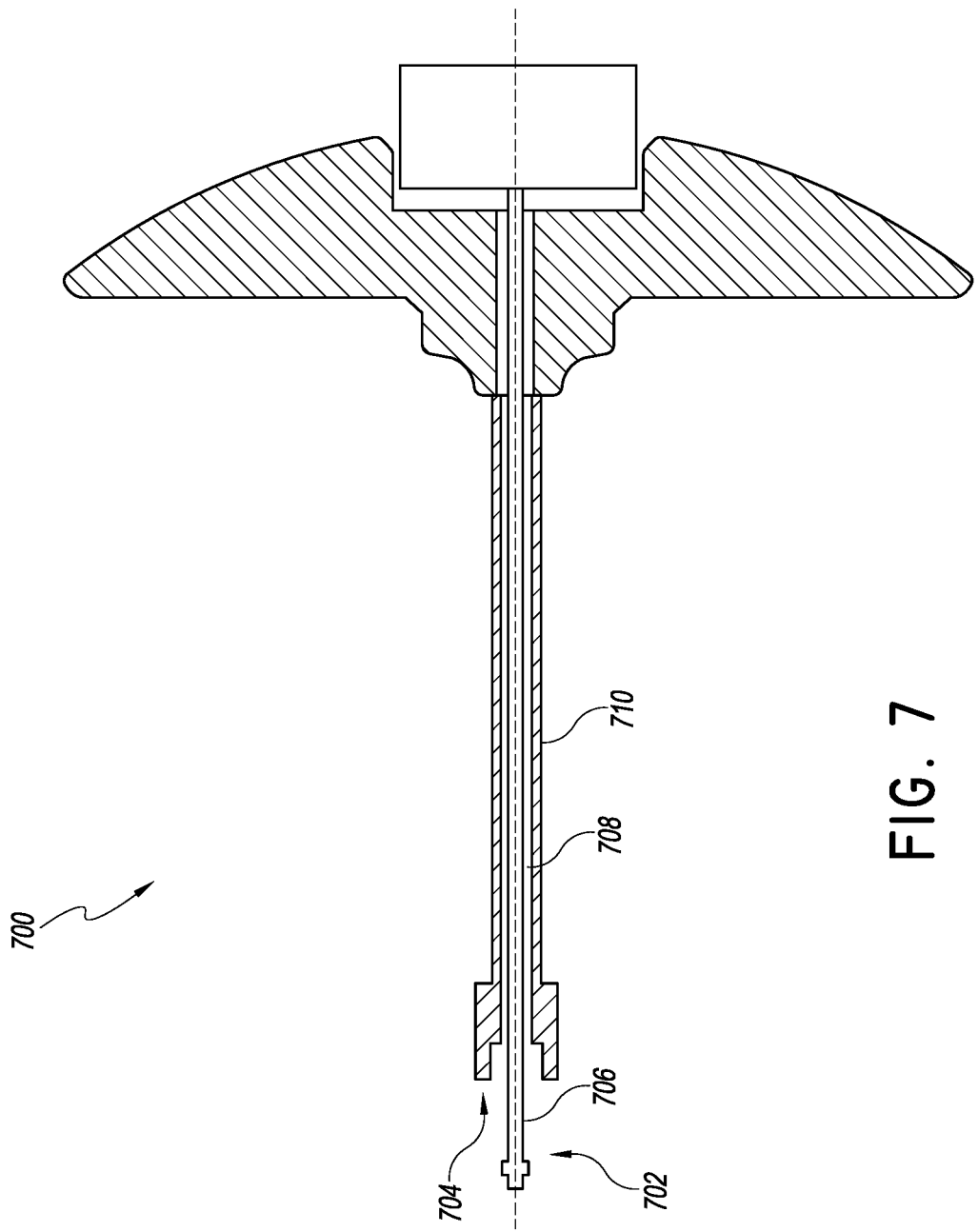
FIG. 7 illustrates a partial cross-sectional view of one embodiment of an implantation tool which can be used to convert an intervertebral cage apparatus from an undeployed position to a deployed position.

For example, as illustrated in FIG. 7, the distal part 702 of the implantation device 700 can be used to engage the front surface of the front panel 102 or an edge forming the aperture 118. A proximal part 704 of the implantation device 700 can then be used to grasp a portion of the circuitous body 105. For example, the proximal part of the implantation device 700 can engage the top panel 150 and the bottom panel 160 using clips, prongs or similar devices. The distal part 702 can be movable relative to the proximal part 704. As shown in the illustrated embodiment, the distal part 702 can be formed on an inner shaft 706 which is translatable within a lumen 708 of an outer shaft 710 on which the proximal part 704 is formed. Accordingly, a user can maintain the circuitous body 105 in position with the proximal part 704 while retracting the distal part 702 proximally towards the user. In so doing, the user can apply a force onto the front panel 102 towards the circuitous body 105 to transition the intervertebral cage 100 from one configuration to another. The user can also maintain the front panel 102 in position with the distal part 702 while moving the proximal part 704 distally away from the user. In so doing, the user can apply a force onto the circuitous body 105 towards the front panel 102 to transition the intervertebral cage 100. It should be understood that the proximal part 704 of the implantation device 702 can passively or dynamically alter in shape during the transition of the intervertebral cage 100 from one configuration to another configuration. Accordingly, the shape of the proximal part can be altered to match the change in shape of the intervertebral cage 100 while the intervertebral cage 100 transitions between configurations. For example, in some embodiments, the clips or prongs of the implantation device 700 can further separate to accommodate the increase in separation between the top panel 150 and the bottom panel 160 as the intervertebral cage 100 transitions from an undeployed configuration to a deployed configuration.

As another example, after insertion of the guide wire into one or more apertures, the guide wire can be retracted proximally relative to the circuitous body 105 such that a proximally-directed force is applied to the front panel 102. As yet another example, an inflatable device, such as an inflatable bladder, can be placed within the interior volume 190. The inflatable device can be inflated such that the inflatable device increases in volume within the interior volume 190. The inflatable device can contact portions of the intervertebral cage 100 such that a force is applied on the intervertebral cage to deploy the cage 100. Such methods and devices are described in more detail in International Application No. PCT/US2013/056500 filed Aug. 23, 2013, the entire contents of which is hereby incorporated by reference.

In the illustrated embodiment, the top and bottom sections 116a, 116b are generally of rectangular shape notwithstanding the aperture 118. In such a configuration, the top edge 112 and the bottom edge 114 generally remain parallel. In other embodiments, the top and bottom sections are not rectangular shaped but rather wedge shaped such that the top and bottom edges 112, 114 are not parallel. These embodiments can be used when the two surfaces requiring support are oblique and different heights are necessary. Other shapes may include quadrilaterals such as, but not limited to, squares, rectangles, parallelograms, and trapezoids. Shapes may also include polygons with more than four sides, partial ellipses such as semi-circles, and any other shape as may be chosen by one of skill in the art.

Figure 2A:
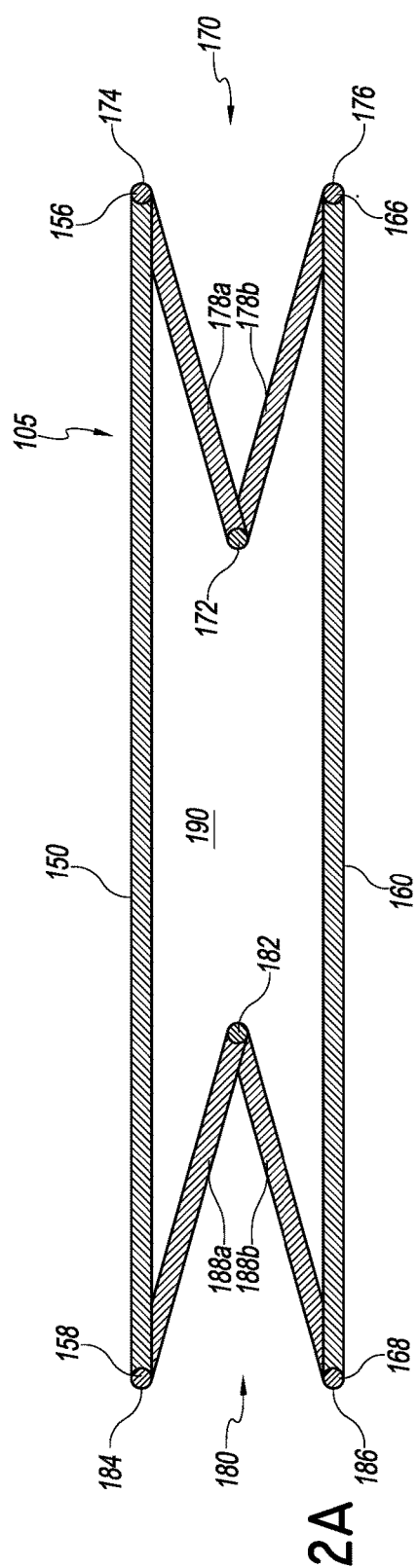
FIG. 2A illustrates a cross-sectional view, along line A-A, of the intervertebral cage of FIG. 1 in a first position.
Figure 2B:
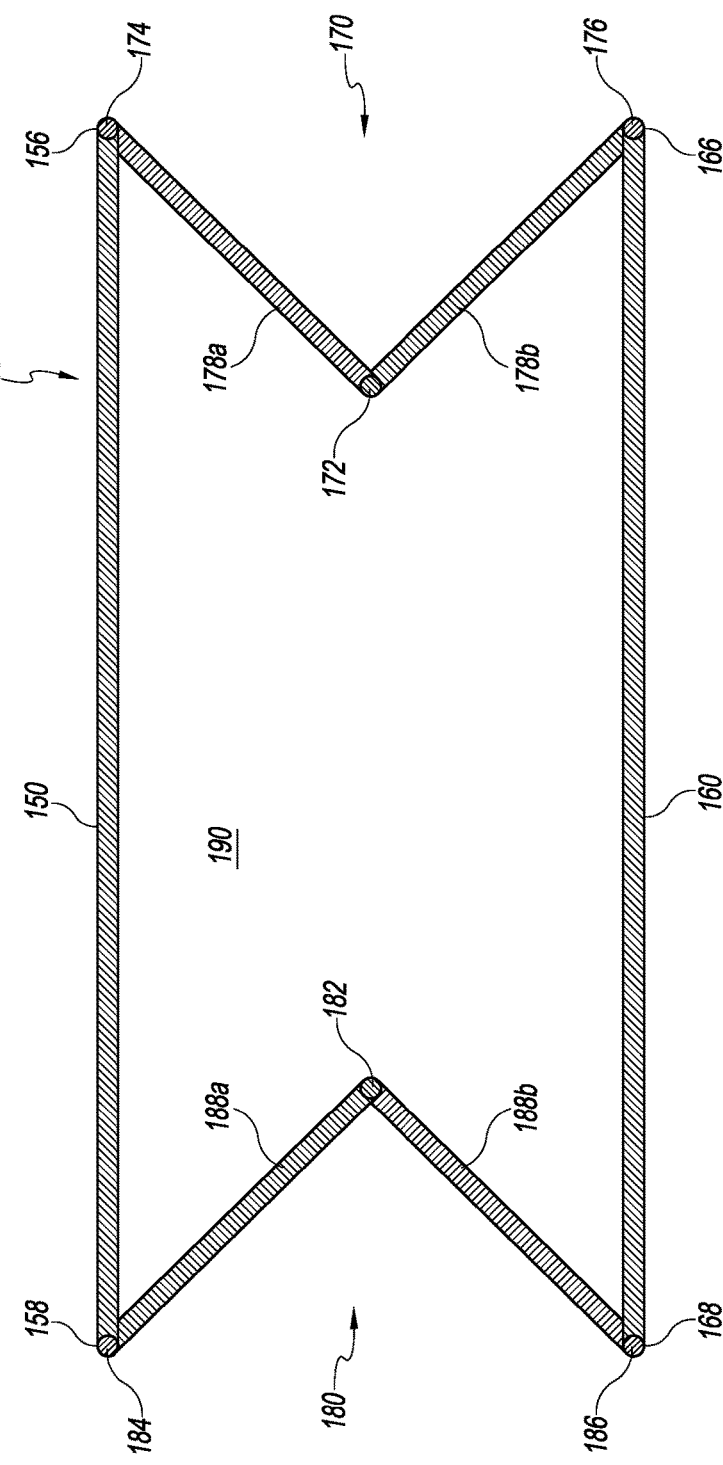
FIG. 2B illustrates a cross-sectional view, along line A-A, of the intervertebral cage of FIG. 1 in a second position.

FIG. 2A-2C are illustrations of a cross-sectional view, as defined in FIG. 1, of an embodiment of the intervertebral cage 100. FIGS. 2A-2C additionally illustrate the process by which the intervertebral cage 100 is converted from the undeployed configuration to the deployed configuration. Three separate configurations are shown: the undeployed configuration (shown in FIG. 2A), an intermediate configuration (shown in FIG. 2B), and the deployed configuration (shown in FIG. 2C). The circuitous body 105 is comprised of a top panel 150, a bottom panel 160, and two side panels 170 and 180. Circuitous body 105 partially encloses an interior volume 190.

In a deployed configuration, top panel 150 is configured to contact and support an end plate of the vertebrae. As such, in some embodiments of the device such as that illustrated in FIG. 1, the top panel 150 is substantially flat. In other embodiments, the top panel 150 can be shaped to better conform to the end plate the panel is configured to contact and support. In yet other embodiments, the top panel 150 may additionally include raised protrusions, ridges or spikes to provide additional stability when the top panel 150 is placed adjacent to and contacting the end plate. In the illustrated embodiment, the top panel 150 includes a distal edge 152, a proximal edge 154, a first side edge 156, and a second side edge 158. In other embodiments, the top panel 150 can be non-rectangular and may include more than four sides. In such embodiments, the cage 100 may have more than two side edges and potentially no proximal edge 154. In other embodiments, the top panel 150 may have one or more apertures configured to facilitate expansion of the cage, to receive bone graft material and/or to promote bone growth between adjacent vertebral bodies. The top panel 150 may also include one or more screw holes configured to allow attachment of the top panel 150 to the end plate.

In a deployed configuration, bottom panel 160 is configured to contact and support an end plate opposite the end plate supported by the top panel 150. Bottom panel 160 is of similar construction to the top panel 150 although, in some embodiments, the dimensions and shapes may differ based upon the shapes of the end plates the top and bottom panels 150, 160 support. As such, in the illustrated embodiment, the bottom panel has a distal edge 162, a proximal edge 164, a first side edge 156, and a second side edge 158. The bottom panel 160 may also have raised protrusions, ridges or spikes on the surface contacting and supporting the end plate to provide additional stability for the intervertebral cage 100. In other embodiments, the bottom panel 160 may have one or more apertures configured to facilitate expansion of the cage, to receive bone graft material and/or to promote bone growth between adjacent vertebral bodies. The bottom panel 160 may also include one or more screw holes configured to allow attachment of the bottom panel 160 to the end plate.

In a deployed configuration, side panels 170 and 180 are configured to provide structural support, in the form of a strut, for the cage 100. Side panels 170 and 180 are generally of similar construction. Therefore, only side panel 170 will be described in detail with the understanding that side panel 180 can incorporate the same features and embodiments described with respect to side panel 170. It should be noted that, like the top and bottom panels 150, 160, in some embodiments the side panels 170, 180 are of different sizes and shape. In one embodiment, the side panel 170 includes a hinge 172 positioned equidistant from the top edge 174 and the bottom edge 176 which subdivides the side panel 170 into both a top section 178a and a bottom section 178b. In other embodiments, the hinge 172 may be placed closer to the top edge 112 or the bottom edge 114 depending upon the geometry desired when in an undeployed configuration or deployed configuration. Furthermore, in yet other embodiments, more than one hinge can be included on the side panel 170.

In some embodiments, the top section 178a and the bottom section 178b are separate units which are rotatably attached at hinge 172 to form side panel 170. In those embodiments, rotatable attachment of the top and bottom sections 116a, 116b can be accomplished through attachment mechanisms such as, but not limited to, pin-hinge assemblies, elastic adhesives, attachment to other materials allowing for elastic deformation, or other hinging mechanisms used in the art. In another embodiment, the top section 178a and the bottom section 178b are integral and form a single unit. In that embodiment, the hinge 172 is formed via a reduced thickness of the side panel 170 along the hinge 172 which is configured to allow for plastic deformation along hinge 172. In some embodiments, such as the embodiment illustrated in FIG. 1, the side panel 170 is solid and therefore includes no apertures unlike the front panel 102. In other embodiments, the side panel 170 may include one or more apertures. Such apertures may provide a lighter weight intervertebral cage 100 and may also be configured to provide for additional deformation thus changing the support strength along parts of the side panel 170. Additionally, such apertures may also be configured to facilitate expansion of the cage, to receive bone graft material and/or to promote bone growth between adjacent vertebral bodies.

In the illustrated embodiment, the top and bottom sections 178a, 178b are generally rectangular. In such a configuration, the top edge 172 and the bottom edge 174 are parallel. In other embodiments, it may be advantageous to provide sections 178a, 178b in shapes other than rectangles. As one non-limiting example, the top section 178a and bottom section 178b can be wedge shaped such that the vertical dimension at the leading end 106 of the sections is less than the vertical dimension at the trailing end 108 of the sections and vice-versa. As such, in embodiments where the opposite side panel 180 has the same shape, the intervertebral cage 100 can have a wedge shape which may be more advantageous in situations where the two endplates to be supported are oblique rather than parallel. Other potential shapes may include quadrilaterals such as, but not limited to, squares, rectangles, parallelograms, and trapezoids. Shapes may also include polygons with more than four sides, partial ellipses such as semi-circles, and any other shape as may be chosen by one of skill in the art.

With reference to FIG. 1, front panel 102 is connected to the circuitous body 105. The top edge 112 of the front panel 102 is rotatably attached to the distal edge 152 of the top plate 150 and the bottom edge 114 of the front panel 102 is rotatably attached to the distal edge 162 of the bottom plate 160 thereby forming hinges along these edges. As such, in some embodiments, the front panel 102 may be a separate unit from the top panel 150 and the bottom panel 160. In those embodiments, the front panel 102 is rotatably attached to the panels 150, 160 via mechanisms such as, but not limited to, pin-hinge assemblies, elastic adhesives, attachment to other materials allowing for elastic deformation, or other hinging mechanisms used in the art. In other embodiments, the front panel 102 may be a single, integral unit with either the top panel 150, the bottom panel 160, or both. In such embodiments, the hinge between the integral unit may be a living hinge. Furthermore, in such embodiments where the integral unit is separate from the top or bottom panels 150, 160, the hinge between the integral unit and the separate unit may be any of the attachment mechanisms described above.

With reference to FIGS. 2A-2C, side panel 170 is connected to the top panel 150 and the bottom panel 160. The top edge 174 of the side panel 170 is rotatably attached to the first side edge 156 of the top plate 150 and the bottom edge 176 of the side panel 170 is rotatably attached to the first side edge 166 of the bottom plate 160 thereby forming hinges along these edges. In some embodiments, the side panel 170 may be a separate unit from the top panel 150 and the bottom panel 160. In those embodiments, the side panel 170 is rotatably attached to the panels 150, 160 via mechanisms such as, but not limited to, pin-hinge assemblies, elastic adhesives, attachment to other materials allowing for elastic deformation, or other hinging mechanisms used in the art. In other embodiments, the side panel 170 may be a single, integral unit with either the top panel 150, the bottom panel 160, or both. In such embodiments, the hinge between the integral unit may be a living hinge. Furthermore, in such embodiments where the integral unit is separate from the top or bottom panels 150, 160, the hinge between the integral unit and the separate unit may be any of the attachment mechanisms described above.

The connection between side panel 180 and the top and bottom panels 150, 160 is similar to that of the side panel 170. The top edge 184 of the side panel 180 is rotatably attached to the second side edge 158 of the top plate 150 and the bottom edge 186 of the side panel 180 is rotatably attached to the second side edge 168 of the bottom plate 160 thereby forming hinges along these edges. In some embodiments, the side panel 180 may be a separate unit from the top panel 150 and the bottom panel 160. In those embodiments, the side panel 180 is rotatably attached to the panels 150, 160 via mechanisms such as, but not limited to, pin-hinge assemblies, elastic adhesives, attachment to other materials allowing for elastic deformation, or other hinging mechanisms used in the art. In other embodiments, the side panel 180 may be a single, integral unit with either the top panel 150, the bottom panel 160, or both. In such embodiments, the hinge between the integral unit may be a living hinge. Furthermore, in such embodiments where the integral unit is separate from the top or bottom panels 150, 160, the hinge between the integral unit and the separate unit may be any of the attachment mechanisms described above.

Therefore, it should be apparent to one of skill in the art that the panels of the intervertebral cage 100 could form integral units with adjacent panels through the use of a living hinge or could be separate from adjacent units and rotatably attached via attachment mechanisms described above. In some embodiments of the device, both living hinges and other attachment mechanisms are simultaneously used. This could allow the device to be assembled post-manufacturing and potentially provide cost savings. In other embodiments, living hinges are used throughout the entire device. This could allow the device to have a more compact profile while in the undeployed state. In yet other embodiments, no living hinges are used. In such embodiments, all pieces could be manufactured separately and allow for a user of the cage 100 to mix different panel shapes and sizes together to obtain a desired shape and size.

In one embodiment, the panels of the intervertebral cage 100 are manufactured from polyetheretherketone (PEEK) or similar biomaterials having shape memory characteristics. In other embodiments, the panels are manufactured from other materials such as, but not limited to, metals including titanium, stainless steel, nitinol, and pyrolitic carbon, medical grade polymers such as PEEK and silicone, and other biocompatible materials known in the art. In yet other embodiments, the panels may be manufactured from different types of materials. As one non-limiting example, the front panel 102 and side panels 170, 180 may be manufactured from a metal such as titanium to provide a lightweight yet rigid support structure while the top and bottom panels 150, 160 may be manufactured from PEEK or other types of materials which may better conform to and support the end plates. The types of materials used for the separate panels may be mixed to obtain the desired structural and performance characteristics of the device.

Operation

As discussed above, the panels and sections of the intervertebral cage 100 are rotatably attached to adjacent panels and sections. As such, the separate panels of the intervertebral cage 100 can rotate from an undeployed configuration to a deployed configuration. The process of converting from the undeployed configuration to a deployed configuration of one embodiment of the intervertebral cage 100 is illustrated in FIGS. 2A-2C and 3A-3C.

FIGS. 3A-3C is a view from the left side of the intervertebral cage 100 which illustrates one non-limiting method of converting the intervertebral cage 100 from an undeployed configuration to a deployed configuration. Three separate configurations are shown: the undeployed configuration (shown in FIG. 3A), an intermediate configuration (shown in FIG. 3B), and the deployed configuration (shown in FIG. 3C).

With reference to FIG. 3A, while in the undeployed configuration, the front panel 102 is collapsed such that top section 116a and bottom section 116b form the sides of a wedge with hinge 110 forming the tip of the wedge. In this embodiment, the hinge 110 extends outwardly in a distal direction thereby providing the intervertebral cage 100 with a wedge-shaped or tapered leading end 106. During an implantation procedure, since the front panel 102 is the initial portion of the intervertebral cage 100 that enters the surgical site and the vertebral space, this wedge-shaped or tapered configuration facilitates insertion of the intervertebral cage 100 into the patient during an implantation procedure. First, because of the wedge shape, the user is assisted in centering the cage 100 within the space formed by the two vertebral end plates as the user advances the cage 100 into this space. Second, since the intervertebral cage 100 is at a reduced height in the undeployed configuration, there is a reduced likelihood that portions of the cage 100, such as the top and/or bottom panels 150, 160, will contact the end plates thereby hindering advancement of the cage 100 during the procedure.

With reference to FIG. 2A, while in the undeployed configuration, the side panels 170, 180 are collapsed inwardly such that they extend into the interior volume 190 of the circuitous body 105. Collapsing inwardly provides the advantage of minimizing the width of the cage 100 during an implantation procedure thereby potentially reducing the size of the surgical site and the overall invasiveness of the procedure. A reduced width also provides the benefit of reducing the likelihood that the side panels 170 and 180 will contact other parts of the spinal column during the implantation procedure. As such, the reduced width facilitates maneuvering the device around to the desired placement area. In other embodiments, the side panels 160, 170 extend outwardly away from the interior volume 190 when in the undeployed configuration. Extending outwardly provides the potential advantage of allowing a further reduced vertical dimension of the cage 100 while in the undeployed configuration.

In some embodiments, conversion the device from the undeployed configuration to the deployed configuration can be performed by applying a force 300, in the direction of the trailing edge 108, to the front panel 102. This can be accomplished by pulling the front panel 102 while inhibiting any translation of the device in a plane parallel to the vertebral end plates (i.e., by applying, for example, a counter-force on the top and bottom plates 150, 160). Due to both the force on the front panel 102 and the rotatable attachment of the top and bottom sections 116a, 116b, the hinge 110 is pulled towards the trailing end 108. This motion increases the angle formed between the top section 116a and the bottom section 116b thereby causing a vertical expansion of the cage 100. An illustration of the movement of the front panel 102 and top and bottom panels 150, 160 can be observed in FIGS. 3A-3C. Because the side panels 160, 170 are rotatably attached to the top and bottom panels 150, 160, the side panels 160, 170 are forced to rotate outwardly and away from the interior volume 190. An illustration of the movement of the side panels 170, 180 and top and bottom panels 150, 160 can be observed in FIGS. 2A-2C.

Note that the cage 100 can also be opened using other methods. As one non-limiting example, a force can instead be placed on the circuitous body 105 towards the leading end 106 while inhibiting the front panel 102, or more specifically the hinge 110, from translating in the same direction. As a second non-limiting example, the forces may instead be applied to the side panels 160, 170 in a direction opposite that in which they are collapsed. Thus, if collapsed inwardly towards the interior volume 190, the separate forces can be applied on each side panel in a direction away from the interior volume 190. If collapsed outwardly away from the interior volume 190, the separate forces can be applied on each side panel in a direction towards the interior volume 190. As a third non-limiting example, an upwards vertical force may be applied to the bottom surface of the top panel 150 and a downwards vertical force may be applied to the top surface of the bottom panel 160 to commence the conversion process. Some or all of the methods described above can be combined together during the process of converting the cage 100 from an undeployed configuration to a deployed configuration.

Hinge Mechanisms/Lock Mechanisms

In some embodiments, in order to reduce the likelihood that the intervertebral cage 100 will revert from the deployed configuration to the undeployed configuration when already implanted, a locking mechanism is used.

Figure 4B:
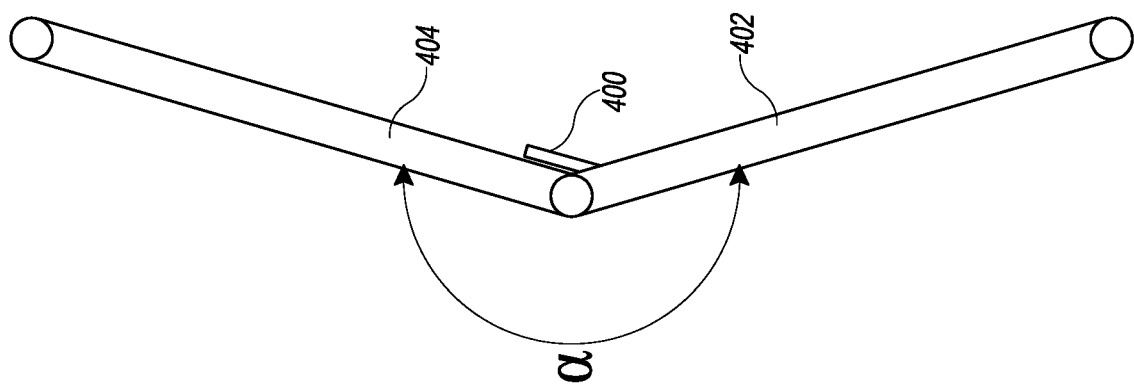
FIG. 4B illustrates a side elevation view of the hinge and locking mechanism of FIG. 4A in a second position.
Figure 4A:
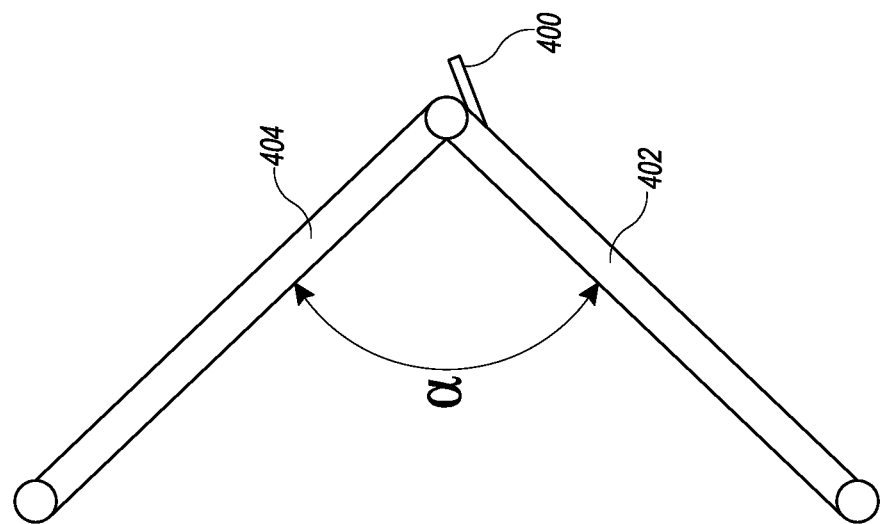
FIG. 4A illustrates a side elevation view of an embodiment of a hinge and locking mechanism in a first position.

In some embodiments, the locking mechanism is configured to reduce the range of motion of the hinges, such as, but not limited to, the hinges 110, 162, and 172 of the front panel 102, side panel 160, and side panel 170 respectively and is placed directly on the panel to reduce over-rotation of a rotatable panel. FIGS. 4A and 4B are illustrations of one embodiment of a locking mechanism configured to reduce the range of motion of the hinges. In this embodiment, a protrusion 400 is placed on the interior surface of one section 402 of the rotating panel. Upon being rotated to a desired angle, the protrusion 400 contacts the adjacent section 404 thereby providing resistance against additional rotation in that direction. In some embodiments, the angle α is slightly greater than 180° to reduce the likelihood that the device will rotate in the reverse direction and revert back to the undeployed configuration.

Figure 5B:
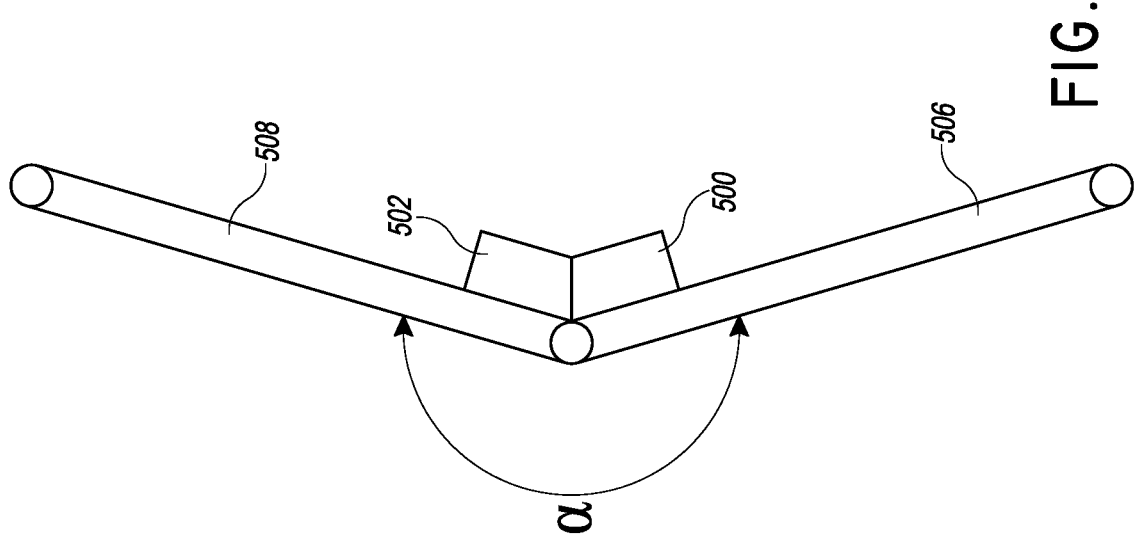
FIG. 5B illustrates a side elevation view of the hinge and locking mechanism of FIG. 5A in a second position.
Figure 5A:
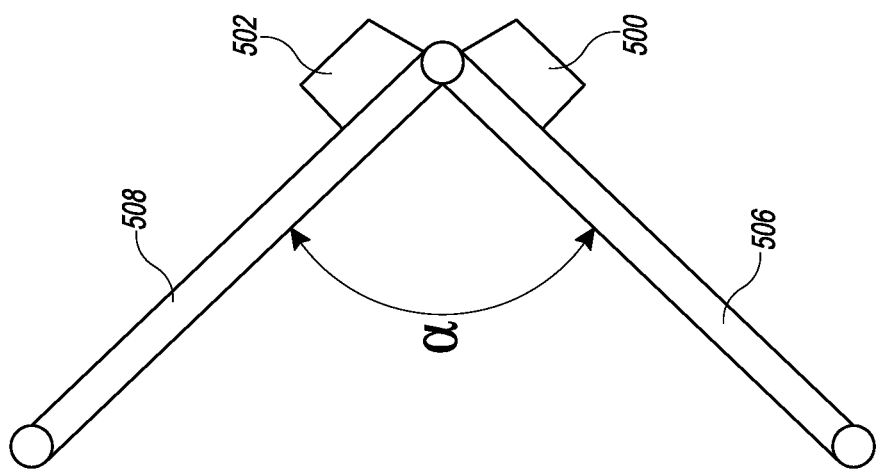
FIG. 5A illustrates a side elevation view of a second embodiment of a hinge and locking mechanism in a first position.

FIGS. 5A and 5B are illustrations of a second embodiment of a locking mechanism configured to reduce the range of motion of the hinges. In this embodiment, there are two protrusions 500 and 502 located on inner surfaces of sections 504 and 506 of the rotating panel. The ends of the protrusions are tapered such that, upon rotation of the rotating panel, the protrusions 500 and 502 are placed into contact along the tapered surfaces thereby providing resistance against additional rotation in that direction. Like the embodiment described above, in some embodiments, the angle α is slightly greater than 180° to reduce the likelihood that the device will rotate in the reverse direction and revert back to the undeployed configuration. The angle α can be chosen based on the placement of the protrusions 500, 502 and the tapering of the edge.

Figure 6B:
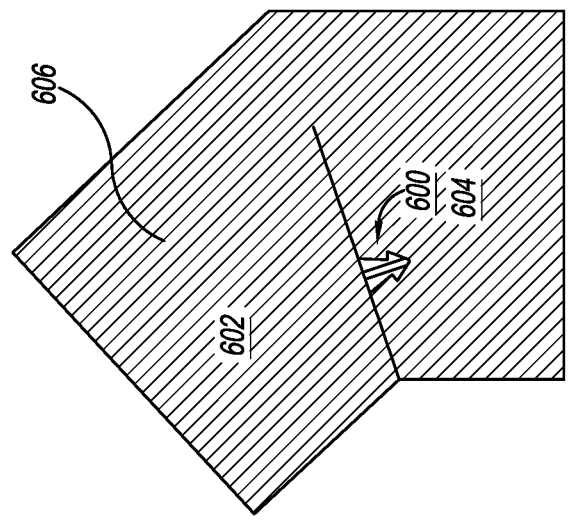
FIG. 6B illustrates a side elevation view of the hinge and locking mechanism of FIG. 6A in a second position.
Figure 6A:
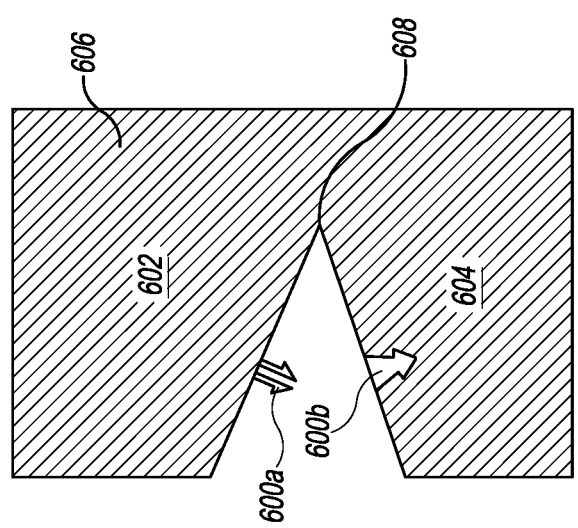
FIG. 6A illustrates a side elevation view of a third embodiment of a hinge and locking mechanism in a first position.

In another embodiment, the hinges 110, 172, and 182 have additional fasteners attached thereto. FIGS. 6A and 6B are illustrations of an embodiment of a fastener 600. A male portion 600a of the fastener 600 is placed on one section 602 and is configured to be inserted into a female portion 600b located on a second section 604 of the rotatable panel 606. Upon being sufficiently rotated about the hinge 608, the male portion 600a is received in the female portion 600b and, due to the shape of the fastener, provides resistance against being removed. As such, rotation in the opposite direction is reduced by virtue of the fastener 600. Note that, although these locking mechanisms were discussed with respect to hinges 110, 172, and 182, these mechanisms may also be used for any other hinge located on the intervertebral cage 100.

In some embodiments, the range of motion of the hinges, such as, but not limited to, the hinges 110, 162, and 172 of the front panel 102, side panel 160, and side panel 170 respectively is reduced by placing rigid clips connecting different panels and/or sections together. In yet other embodiments, the range of motion of the hinges can be reduced by inserting an additional member into the interior volume 190 of the circuitous body 105. In yet another embodiment, the range of motion of the hinges can be reduces through the use of screws.

In order to inhibit translation of the intervertebral cage 100 after it has been inserted into and deployed within the vertebral space, other fastening mechanisms can be used to attach the cage 100 to the end plates. In one embodiment, screws can be inserted through screw holes located on the top panel 150 and bottom panel 160 into the upper and lower vertebral bodies, respectively. Such screws may pass though screw holes that are angled upward and downward into the respective vertebral bodies from the rear of the intervertebral cage.

Optional Back Panel

Intervertebral cage 100 may additionally include a back panel to close the trailing end 108 of the cage 100. In one embodiment, the back panel is configured to be inserted into the interior volume 190 of the circuitous body 105. By being inserted into the circuitous body 105, the back panel provides additional support for the cage 100 and can serve the additional function of preventing the cage 100 from reverting from the deployed configuration to the undeployed configuration. In some embodiments, the back panel additionally comprises a spring element which, when inserted into the interior volume 190, provides an additional elastic support for the two intervertebral end plates.

In another embodiment, the back panel is attached directly to the top panel 150 and the bottom panel 160 after the intervertebral cage 100 has been deployed in the vertebral space. In such embodiments, the back panel may be attached to the proximal edge 154 of the top panel 150 and the proximal edge 164 of the bottom panel 160. The back panel may also additionally be attached to the side panels 160 and 170 as an additional means of reducing the range of motion of the hinges. In yet other embodiments, the back panel may be initially rotatably attached to either the proximal edge 154 or the proximal edge 164 prior to insertion into the vertebral space. In such embodiments, upon deploying the vertebral cage 100, the back panel may be rotated about the edge to which it is rotatably attached and additionally attach to the opposite proximal edge.

In some embodiments, the back panel is of similar construction to the front panel 102 and is initially attached to both the top panel 150 and the bottom panel 160. In the above-mentioned embodiments, the back panel may also include apertures configured to facilitate expansion of the cage, to receive bone graft material and/or to promote bone growth between adjacent vertebral bodies.

Although the methods and devices are described above with respect to a use within the intervertebral space for supporting two end plates, the device can be used with other portions of the body and in other procedures. Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein.

List of Embodiments

1. A vertically expandable intervertebral cage configured to be inserted between two vertebral endplates, comprising:
   a circuitous body at least partially enclosing an interior volume, the circuitous body comprising:
   a top panel, having a distal edge and at least two side edges;
   a bottom panel, having a distal edge and at least two side edges; and
   at least two side panels, each having a top edge and a bottom edge, wherein the side panel comprises at least one hinge dividing the side panel into at least two side panel sections;
   wherein the top edges of the side panels are rotatably attached to the side edges of the top panel along a hinge and the bottom edges of the side panels are rotatably attached to the side edges of the bottom panel along a hinge; and
   a front panel, having a top edge and a bottom edge, wherein the front panel additionally comprises at least one hinge dividing the front panel into at least two front panel sections;
   wherein the top edge of the front panel is rotatably attached to the distal edge of the top panel and the bottom edge of the front panel is rotatably attached to the distal edge of the bottom panel;
   wherein, in a first position, the top panel and bottom panel are separated by a first distance and the front panel forms a leading wedge; and
   wherein, in a second position, the top panel and bottom panel are separated by a second distance, the second distance being greater than the first distance.

2. The vertically expandable intervertebral cage of embodiment 1, wherein at least one of the hinges comprise a living hinge.

3. The vertically expandable intervertebral cage according to any of embodiments 1 and 2, further comprising a locking mechanism configured to reduce the range of motion of at least one hinge.

4. The vertically expandable intervertebral cage according to any of embodiments 1-3, wherein the locking mechanism comprises a first protrusion along a surface of at least one of the panels.

5. The vertically expandable intervertebral cage of embodiment 4, further comprising a second protrusion along a surface of a panel attached to the panel comprising the first protrusion.

6. The vertically expandable intervertebral cage according to any of embodiments 4 and 5, wherein the protrusion is positioned on an interior surface of the panel.

7. The vertically expandable intervertebral cage according to any of embodiments 1-6, wherein the side panels extend into the interior volume when the intervertebral cage is in the first position.

8. The vertically expandable intervertebral cage according to any of embodiments 1-6, wherein the side panels extend outwardly away from the interior volume when the intervertebral cage is in the first position.

9. The vertically expandable intervertebral cage according to any of embodiments 1-8, wherein, in the second position, the angle formed by the side panel sections is greater than 180 degrees.

10. The vertically expandable intervertebral cage according to any of embodiments 1-9, wherein, in the first position, the at least one hinge of the front panel forms a tip of a wedge 11. The vertically expandable intervertebral cage according to any of embodiments 1-10, wherein at least one of the panels further comprise at least one aperture.

12. The vertically expandable intervertebral cage of embodiment 11, wherein the front panel comprises an aperture.

13. The vertically expandable intervertebral cage of embodiment 11, wherein the front panel comprises two or more apertures.

14. The vertically expandable intervertebral cage according to any of embodiments 1-13, further comprising a back panel for attachment to a trailing end of the intervertebral cage.

15. The vertically expandable intervertebral cage of embodiment 14, wherein the back panel is inserted into the interior volume.

16. The vertically expandable intervertebral cage of embodiment 14, wherein the back panel is attached to the top panel and the bottom panel.

17. The vertically expandable intervertebral cage according to any of embodiments 1-13, wherein at least one panel comprises polyetheretherketone (PEEK).

18. A vertically expandable intervertebral cage, comprising:
- a circuitous body comprised of a plurality of panels partially enclosing an interior volume, the plurality of panels comprising at least a top panel, a bottom panel, and two side panels, wherein each of the panels comprising the plurality of panels are rotatably attached to adjacent panels along hinges; and
- a front panel comprising a first front panel section rotatably attached to a second front panel section, the front panel being rotatably attached to at least two panels of the plurality of panels of the circuitous body;
- wherein, in a first position, a distal-most part of the front panel protrudes distally from the circuitous body, and
- wherein, in a second position, the distal-most part of the front panel protrudes less distally from the circuitous body.

19. The vertically expandable intervertebral cage of embodiment 18, wherein:
- in the first position, a first angle is formed between the first front panel section and the second front panel section, and
- in the second position, a second angle is formed between the first front panel section and the second front panel section, the second angle being greater than the first angle.

20. The vertically expandable intervertebral cage according to any of embodiments 18 and 19, wherein the front panel forms a leading wedge while the cage is in the first position.

21. The vertically expandable intervertebral cage according to any of embodiments 18-20, the two side panels each comprise a first side panel section rotatably attached to a second side panel section.

22. The vertically expandable intervertebral cage of embodiment 21, wherein the side panels expand outwardly from the interior volume when the intervertebral cage is transitioned from the first position to the second position.

23. The vertically expandable intervertebral cage of embodiment 22, wherein, in the second position, the angle formed by the side panel sections is greater than 180 degrees.

24. The vertically expandable intervertebral cage of embodiment 21, wherein the side panels expand inwardly towards the interior volume when the intervertebral cage is transitioned from the first position to the second position.

25. The vertically expandable intervertebral cage according to any of embodiments 18-24, wherein at least one of the panels further comprise at least one aperture.

26. The vertically expandable intervertebral cage of embodiment 25, wherein the front panel comprises an aperture.

27. The vertically expandable intervertebral cage of embodiment 25, wherein the front panel comprises two or more apertures.

28. The vertically expandable intervertebral cage according to any of embodiments 18-27, wherein at least one panel comprises polyetheretherketone (PEEK).

29. A method of deploying an intervertebral cage within an intervertebral disc space, the method comprising:
- positioning the intervertebral cage in the intervertebral disc space, wherein the intervertebral cage is configured to be moved from a first position to a second position and wherein the intervertebral cage comprises a circuitous body and a front panel;
- forming a wedge with the front panel; and
- applying a force on one or more panels of the intervertebral cage,
- wherein the circuitous body comprises a plurality of panels.

30. The method of embodiment 29, wherein the step of applying a force comprises applying a force, in the direction of a trailing edge of the intervertebral cage, to the front panel.

31. The method of embodiment 30, wherein the step of applying a force to the front panel further comprises inhibiting translation of circuitous body.

32. The method of embodiment 29, wherein the step of applying a force comprises applying a force on the circuitous body towards a leading edge of the intervertebral cage.

33. The method of embodiment 32, wherein the step of applying a force to the circuitous body comprises inhibiting translation of circuitous body.

34. The method of embodiment 29, wherein the step of applying a force comprises applying a force on a surface of one or panels in the plurality of panels of the circuitous body.

35. A intervertebral cage system comprising:
an intervertebral cage comprising:
- a circuitous body comprised of a plurality of panels partially enclosing an interior volume, the plurality of panels comprising at least a top panel, a bottom panel, and two side panels, wherein each of the panels comprising the plurality of panels are rotatably attached to adjacent panels along hinges; and
- a front panel comprising a first front panel section rotatably attached to a second front panel section, the front panel being rotatably attached to at least two panels of the plurality of panels of the circuitous body;
- wherein, in a first position, a distal-most part of the front panel protrudes distally from the circuitous body, and
- wherein, in a second position, the distal-most part of the front panel protrudes less distally from the circuitous body; and
a deployment device configured to apply a force to convert the intervertebral cage from the first position to the second position.

36. The system of embodiment 35, wherein:
in the first position, a first angle is formed between the first front panel section and the second front panel section, and
in the second position, a second angle is formed between the first front panel section and the second front panel section, the second angle being greater than the first angle.

37. The system according to any of embodiments 35 and 36, wherein the front panel forms a leading wedge while the cage is in the first position.

38. The system according to any of embodiments 35-37, the two side panels each comprise a first side panel section rotatably attached to a second side panel section.

39. The system of embodiment 38, wherein the side panels expand outwardly from the interior volume when the intervertebral cage is transitioned from the first position to the second position.

40. The system of embodiment 39, wherein, in the second position, the angle formed by the side panel sections is greater than 180 degrees.

41. The system of embodiment 38, wherein the side panels expand inwardly towards the interior volume when the intervertebral cage is transitioned from the first position to the second position.

42. The system according to any of embodiments 35-41, wherein at least one of the panels further comprise at least one aperture.

43. The system of embodiment 42, wherein the front panel comprises an aperture.

44. The system of embodiment 42, wherein the front panel comprises two or more apertures.

45. The system according to any of embodiments 35-44, wherein at least one panel comprises polyetheretherketone (PEEK).

46. The system according any of embodiments 35-44, wherein the deployment device comprises an implantation device.

47. The system according to any of embodiments 35-44, wherein the deployment device comprises a guide wire.

What is claimed is:

1. A vertically expandable intervertebral cage configured to be inserted between two vertebral endplates, comprising:
    a body at least partially enclosing an interior volume, the body comprising:
        a top panel having a distal edge, a proximal edge and at least two side edges;
        a bottom panel having a distal edge, a proximal edge and at least two side edges, wherein the distal edges of the top and bottom panels both lie within a front plane;
        at least two integral side panels, each having a top edge and a bottom edge, wherein the side panel comprises a living hinge dividing the side panel into a top side section and a bottom side section, the top and bottom edges of the side panels being rotatably attached to the side edges of the top and bottom panels along a living hinge;
        an integral front panel, having a top edge and a bottom edge, wherein the front panel comprises a living hinge dividing the front panel into a top front panel section and a bottom front panel section, the top and bottom edges of the front panel being rotatably attached to the distal edges of the top and bottom panels along a living hinge;
        an integral back panel, having a top edge and a bottom edge, wherein the back panel comprises a living hinge dividing the back panel into a top back panel section and a bottom back panel section, the top and bottom edges of the back panel being rotatably attached to the proximal edges of the top and bottom panels along a living hinge;
    wherein, in a first position, the top panel and bottom panel are separated by a first distance and the living hinge of the top and bottom front panel sections of the front panel extends away from the front plane and forms a leading wedge; and
    wherein, in a second position, the top panel and bottom panel are separated by a second distance, the second distance being greater than the first distance.

2. The vertically expandable intervertebral cage of claim 1, wherein the top and bottom back sections of the side panels and back panel extend into the interior volume when the intervertebral cage is in the first position.

3. The vertically expandable intervertebral cage of claim 1, wherein the top and bottom back sections of the side panels and back panel extend outwardly away from the interior volume when the intervertebral cage is in the first position.

4. The vertically expandable intervertebral cage of claim 1, wherein the front panel comprises at least one aperture.

5. The vertically expandable intervertebral cage of claim 1, wherein the back panel comprises at least one aperture.

6. The vertically expandable intervertebral cage of claim 1, wherein the top patent and/or bottom panel includes raised protrusions, ridges or spikes configured to provide additional stability when the panels are placed adjacent to and contacting the vertebral endplates.

7. The vertically expandable intervertebral cage of claim 1, wherein the top and/or bottom panels are configured to be shaped to conform to the vertebral endplates the panel is configured to contact and support.

8. The vertically expandable intervertebral cage of claim 1, wherein the top and bottom panels include one or more screw holes configured to allow attachment of the top and bottom panels to the two vertebral endplates.

9. The vertically expandable intervertebral cage of claim 1, further comprising an implantation device having a distal part configured to engage the front panel and a proximal part configured to grasp a portion of the body, the implantation device being configured to apply a force to transition the intervertebral cage from first position to the second position.

10. The vertically expandable intervertebral cage of claim 1, further comprising a guide wire configured to engage the front panel and retracted proximally relative to the body such that a proximally-directed force is applied to the front panel to convert the intervertebral cage from first position to the second position.

11. The vertically expandable intervertebral cage of claim 1, further comprising an inflatable device configured to be placed within the interior volume be inflated to apply a force to convert the intervertebral cage from the first position to the second position.

12. A vertically expandable intervertebral cage, comprising:
    a body comprised of a plurality of panels partially enclosing an interior volume, the plurality of panels comprising at least a top panel having a distal edge, a bottom panel having a distal edge, wherein the distal edges of the top and bottom panels both lie within a front plane, and two integral side panels, wherein each of the side panels comprising top and bottom side sections rotatably attached to adjacent panels along living hinges; and
    an integral front panel comprising a top front panel section rotatably attached by a living hinge to a bottom front panel section, the front panel being rotatably attached by living hinges to at least two panels of the plurality of panels of the body;
    an integral back panel comprising a top back panel section rotatably attached by a living hinge to a bottom back panel section, the back panel being rotatably attached by living hinges to at least two panels of the plurality of panels of the body;

wherein, in a first position, the living hinge of the front panel extends away from the front plane forming a wedge, and wherein, in a second position, the living hinge of the front panel extends away less from the front plane.

13. The vertically expandable intervertebral cage of claim 12, wherein the top and bottom back sections of the side panels and back panel extend into the interior volume when the intervertebral cage is in the first position.

14. The vertically expandable intervertebral cage of claim 12, wherein the top and bottom back sections of the side panels and back panel extend outwardly away from the interior volume when the intervertebral cage is in the first position.

15. The vertically expandable intervertebral cage of claim 12, further comprising an implantation device having a distal part configured to engage the front panel and a proximal part configured to grasp a portion of the body, the implantation device being configured to apply a force to transition the intervertebral cage from first position to the second position.

16. The vertically expandable intervertebral cage of claim 12, further comprising a locking mechanism configured to reduce the range of motion of at least one hinge.

17. A method of vertically deploying an intervertebral cage within an intervertebral disc space, the method comprising:

positioning the intervertebral cage in the intervertebral disc space, wherein the intervertebral cage is configured to be moved from a first position to a second position and wherein the intervertebral cage comprises a body at least partially enclosing an interior volume, the body comprising;

a top panel, having a distal edge and at least two side edges;

a bottom panel, having a distal edge and at least two side edges, wherein the distal edges of the top and bottom panels both lie within a front plane; and at least two integral side panels, each having a top edge and a bottom edge, wherein the side panel comprises at least one a living hinge dividing the side panel into a top side section and a bottom side section; and an integral front panel, having a top edge and a bottom edge, wherein the front panel additionally comprises a living hinge dividing the front panel into a top front panel section and a bottom front panel section;

an integral back panel, having a top edge and a bottom edge, wherein the back panel additionally comprises a living hinge dividing the back panel into a top front panel section and a bottom front panel section;

wherein, in a first position, the living hinge of the front panel extends away from the front plane forming a wedge, and wherein, in a second position, the living hinge of the front panel extends away less from the front plane;

applying a force on one or more panels of the intervertebral cage, and vertically expanding the intervertebral cage within the intervertebral disc space from the first position to the second position, wherein, in the first position, the top panel and bottom panel are separated by a first distance, and in the second position, the top panel and bottom panel are separated by a second distance, the second distance being greater than the first distance.

18. The method of claim 17, wherein applying a force on one or more panels of the intervertebral cage incudes an implantation device having a distal part configured to engage the front panel and a proximal part configured to grasp a portion of the body, the implantation device being configured to apply the force to transition the intervertebral cage from first position to the second position.

19. The method of claim 17, further comprising shaping the top and/or bottom panels to conform to vertebral endplates the panel is configured to contact and support.

20. The method of claim 17, wherein the body further includes a locking mechanism, and the method further comprises locking the body in the second position.

* * * * *